(12) United States Patent
Priestly et al.

(10) Patent No.: US 8,260,028 B2
(45) Date of Patent: Sep. 4, 2012

(54) OFF-AXIS SHEET-HANDLING APPARATUS AND TECHNIQUE FOR TRANSMISSION-MODE MEASUREMENTS

(75) Inventors: Richard Sean Priestly, Painted Post, NY (US); Eric Alfred Soehnlein, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 531 days.

(21) Appl. No.: 12/607,346

(22) Filed: Oct. 28, 2009

(65) Prior Publication Data

US 2011/0096978 A1    Apr. 28, 2011

(51) Int. Cl.
*G06K 9/00* (2006.01)
(52) U.S. Cl. ........................................................ 382/141
(58) Field of Classification Search .................. 382/141
See application file for complete search history.

(56) References Cited

U.S. PATENT DOCUMENTS

| 3,665,730 | A |   | 5/1972 | Linzer ........................ 65/182 A |
| 5,311,276 | A |   | 5/1994 | Masao et al. .................. 356/239 |
| 5,452,079 | A | * | 9/1995 | Okugawa ................... 356/239.1 |
| 2008/0204741 | A1 |   | 8/2008 | Hill et al. .................... 356/239.7 |

FOREIGN PATENT DOCUMENTS

| JP | 2004/203668 | 7/2004 |
| JP | 2004/251723 | 9/2004 |
| JP | 2006/242714 | 9/2006 |
| WO | 2004/089792 | 10/2004 |

* cited by examiner

*Primary Examiner* — Roy M Punnoose
(74) *Attorney, Agent, or Firm* — Jeffrey A. Schmidt

(57) ABSTRACT

An apparatus (2) and method, for measuring process-induced features in a transparent sheet (10). The apparatus includes a light source (100), an imaging device (80), and a support structure (30) disposed between the light source and the imaging device. The support structure is configured and arranged to support the transparent sheet so that measurement error induced by the support structure is viewed by the imaging device as extending along or parallel to a first axis (46, 54) that is oblique to a second axis (22, 24) along or parallel to which the process-induced features in the transparent sheet extend when viewed by the imaging device.

20 Claims, 5 Drawing Sheets

OFF-AXIS SHEET-HANDLING APPARATUS AND TECHNIQUE FOR TRANSMISSION-MODE MEASUREMENTS

BACKGROUND

1. Field

The present invention relates to support structures and methods for handling thin sheets during inspection, and particularly for handling thin transparent sheets during transmission-mode measurements

2. Technical Background

Recently, significant attention has been focused on the detection of defects in transparent substrates, for example glass sheets, primarily due to the popularity and acceptance of the liquid crystal display (LCD) television. As such, the industry is now challenged with meeting increased volume demands while delivering substrates that comply with stringent LCD transmission-mode specifications. Additionally, the transparent sheets used in the LCD industry have been growing in size while, at the same time, remaining the same thickness or even becoming thinner. Accordingly, it is a challenge to hold a large, thin, transparent sheet securely so that inspection measurements may be made, while at the same time maintaining measurement accuracy in light of errors induced by the structure used to hold the transparent sheet.

Transmission mode measurements include passing light through the transparent sheet from one planar face to the opposite planar face, and measuring how the light changes as it passes through. Transmission mode measurements may be used to detect process-induced features like inclusions, thickness variations, cord, streak, and stress, for example, in the transparent sheet.

Taking stress measurements for example, the manner in which the sheet is held will affect the measurement because stress may be induced by the interaction of the holding structure and the shape of the sheet. If a sheet were completely flat, its shape would not change when held in a substantially planar configuration by a holding structure and, accordingly, the holding structure would not affect the stress measurement. However, transparent sheets are not completely flat; instead, they include some (albeit small in most instances in the display industry) shape variance as, for example, warp, bow, convexity, or concavity, which is not likely to be the same from sheet to sheet. Further, such shape variance may be included in varying degrees in different areas of the sheet. Accordingly, when a transparent sheet is flattened by a holding structure during measurement, the sheet shape changes, which introduces errors in transmission-mode measurement. For example, the transparent sheet, in its nominal resting state, includes a stress distribution which affects light transmittance through the sheet. When the sheet is flattened, as in a support structure, the stress distribution changes so as also to include stress induced by the support structure when flattening the sheet. Thus, accuracy of the sheet stress measurement is affected. It is desirable to account for and remove the inaccuracy induced by the support structure to the extent possible. However, it is not always easy to differentiate what stress is induced by the support structure, and what stress is naturally occurring in the transparent sheet.

In light of the above, there is a need for an inspection method and apparatus which can hold large, thin, transparent substrates securely, allow support-structure-induced error easily to be detected accounted for and removed to the extent possible.

SUMMARY

The present application describes an apparatus and technique for making transmission mode measurements of a sheet, for example a thin transparent sheet of glass, wherein various features—either taken alone or in various combinations with other features—facilitate: holding the sheet securely so that an accurate measurement can be made; differentiating support-structure induced errors from features of interest in the sheet; quickly making a full-sheet measurement; and measuring various sheet sizes.

Features of an apparatus that can securely hold a thin sheet include: off-axis orientation of the supporting elements relative to the axes of the sheet; support-structure bars, or other supports, that extend along a direction oblique to the cross and down-draw axes of the sheet to be measured; a pressure/vacuum source coupled to the support so as to act on the sheet; and/or that the dimensions of the support are larger than those of the sheet, although this is not necessary. Because the supports extend in a direction oblique to the major axes of the sheet, the supports cross the sheet edges so that only very short sections along the sheet edge are unsupported at any given time, especially during measurement of the process-induced feature in interest. Accordingly, the sheet is held securely.

Features of an apparatus that lead to easy differentiation of support-induced errors from process-induced features of interest include: a support structure configured and arranged to induce measurement error along an axis oblique to that along which process-induced features extend in the sheet; and/or pixels of the image capture units, of the imaging device, that are oriented along axes parallel to the sheet axes and oblique to the support structure axes. Process-induced features typically extend in the direction in which the sheet is formed. In many cases, these features (thickness variations, cord, streak, discontinuities and inclusions within the sheet, and stress, for example), manifest themselves with an orientation matching that in which the transparent sheet was drawn, i.e., in a down-draw direction. In other cases, some features may manifest themselves in a direction perpendicular to that in which the transparent sheet was drawn, i.e., in a cross-draw direction. Accordingly, orienting the support structure so that errors it induces in the measurement extend along an axis oblique to the cross-draw or down-draw axes, facilitates differentiating these errors from the process-induced features of interest that are to be measured.

Features of an apparatus that lead to speed in processing include: that a dimension of the viewing area over which an image of the sheet can be captured is larger than a corresponding dimension of the sheet to be measured by an amount greater than or equal to the dimension of a blocked, or non-image able, area; that the size of the image able areas is greater than that of the non-image able areas; that the supports form an angle of about 25 degrees to about 65 degrees with the sheet transportation direction through the measurement apparatus; and/or that the dimensions of the support are larger than those of the sheet. Accordingly, a sheet can be imaged, indexed by the dimension of the blocked or non-image able area, and imaged again. This facilitates making a full-sheet measurement with as little as two overlaid images, which leads to speed in processing.

Features of an apparatus that make it insensitive to sheet size include that the supports extend along a direction oblique to the major axes of the sheet. Accordingly, because the supports extend diagonally across the sheet and thus need not be spaced with a particular sheet size in mind, the measurement apparatus is largely insensitive to the size of the sheet being measured. Stated another way, with the supports extending oblique to the major axes of the sheet, a support structure can hold stable a sheet section even when the support ranges in size from slightly smaller than the sheet section to much larger than the sheet section.

By way of non-limiting example, the various features may be combined according to the following aspects:

According to a first aspect, there is provided an apparatus, for measuring process-induced features in a transparent sheet, including:

a light source;

an imaging device; and a transparent-sheet support structure disposed between the light source and the imaging device, wherein the support structure is configured and arranged to support a transparent sheet so that measurement error induced by the support structure is viewed by the imaging device as extending along or parallel to a first axis that is oblique to a second axis along or parallel to which the process-induced features in the transparent sheet extend when viewed by the imaging device.

According to a second aspect, there is provided the apparatus of any one of aspects 1, or 3-6, wherein the process-induced feature comprises stress.

According to a third aspect, there is provided the apparatus of aspect 1, wherein the support structure includes bars extending along axes oblique to the second axis.

According to a fourth aspect, there is provided the apparatus of aspect 3, wherein the bars include openings, and the support includes a vacuum source in communication with the openings.

According to a fifth aspect, there is provided the apparatus of aspect 3, wherein spaces are disposed between the bars, wherein the bars include a first width and the spaces include a second width, and further wherein the first width is less than or equal to the second width.

According to a sixth aspect, there is provided the apparatus of aspect 1, wherein the imaging device includes pixels oriented along a third axis, wherein the support structure includes spaces through which light from the light source may be viewed by the imaging device, the spaces including longitudinal axes parallel to the first axis, and further wherein the third axis is oblique to the longitudinal axes.

According to a seventh aspect, there is provided a method of measuring process-induced features in a transparent sheet, including:

disposing a transparent sheet on a support structure that is disposed between a light source and an imaging device;

supporting the transparent sheet so that measurement error induced by the support structure is viewed by the imaging device as extending along or parallel to a first axis that is oblique to a second axis along or parallel to which the process-induced features in the transparent sheet extend when viewed by the imaging device;

capturing a first image of a first section of the transparent sheet;

moving the transparent sheet and then capturing a second image of the first section of the transparent sheet; and combining the first and second images to form an image of the process-induced features in the first section of the transparent sheet.

According to an eighth aspect, there is provided the method of aspect 7, wherein the first and second images together cover the entire area of the first section of the transparent sheet.

According to a ninth aspect, there is provided the method of aspect 8, wherein the first section of the transparent sheet encompasses the entire area of the transparent sheet.

According to a tenth aspect, there is provided the method of any one of aspects 7-9, further including contacting the transparent sheet with a conveyance device during the step of moving, but not during the steps of capturing the first and second images.

According to an eleventh aspect, there is provided the method of any one of aspects 7-10, further including flattening the transparent sheet prior to the steps of capturing the first and second images, and maintaining the transparent sheet in the flattened condition during the steps of capturing the first and second images.

According to a twelfth aspect, there is provided the method of aspect 11, wherein the step of flattening comprises vacuuming the transparent sheet against the support structure.

According to a thirteenth aspect, there is provided the method of aspect 7, wherein the step of combining further comprises removing the measurement error induced by the support structure.

According to a fourteenth aspect there is provided the method of any one of aspects 7-13, wherein the support structure includes bars extending along axes oblique to the second axis, wherein spaces are disposed between the bars, wherein the bars include a first width and the spaces include a second width, and further wherein the first width is less than or equal to the second width.

According to a fifteenth aspect there is provided the method of aspect 14, wherein the imaging device is capable of capturing an image within a viewing area having a third width, the transparent sheet includes a fourth width, and wherein the third width is larger than the fourth width by an amount equal to or greater than the first width.

According to a sixteenth aspect there is provided the method of aspect 15, wherein the support structure includes a fifth width, and the fifth width is larger than the fourth width by an amount equal to or greater than the first width.

According to a seventeenth aspect there is provided the method of aspect 14, wherein the transparent sheet is moved in a transportation direction relative to the support structure, and wherein the axes of the bars form an angle with the transportation direction, the angle ranging from 25 to 65 degrees.

According to an eighteenth aspect there is provided the method of any one of aspects 7-17, wherein the transparent sheet is moved in a direction parallel or perpendicular to the second axis.

According to a nineteenth aspect there is provided the method of any one of aspects 7-18, wherein the imaging device includes pixels extending along a third axis, and further wherein the third axis is oblique to the first axis.

According to a twentieth aspect there is provided the method of any one of aspects 7-18, wherein the process-induced feature comprises stress.

Additional features and advantages will be set forth in the detailed description which follows, and in part will be readily apparent to those skilled in the art from the description or recognized by practicing the invention as exemplified in the written description and the appended drawings. It is to be understood that both the foregoing general description and the following detailed description are merely exemplary of the invention, and are intended to provide an overview or framework to understanding the nature and character of the invention as it is claimed.

The accompanying drawings are included to provide a further understanding of principles of the invention, and are incorporated in and constitute a part of this specification. The drawings illustrate one or more embodiment(s), and together with the description serve to explain, by way of example, principles and operation of the invention. It is to be understood that various features of the invention disclosed in this specification and in the drawings can be used in any and all combinations.

DETAILED DESCRIPTION

Figure 1:
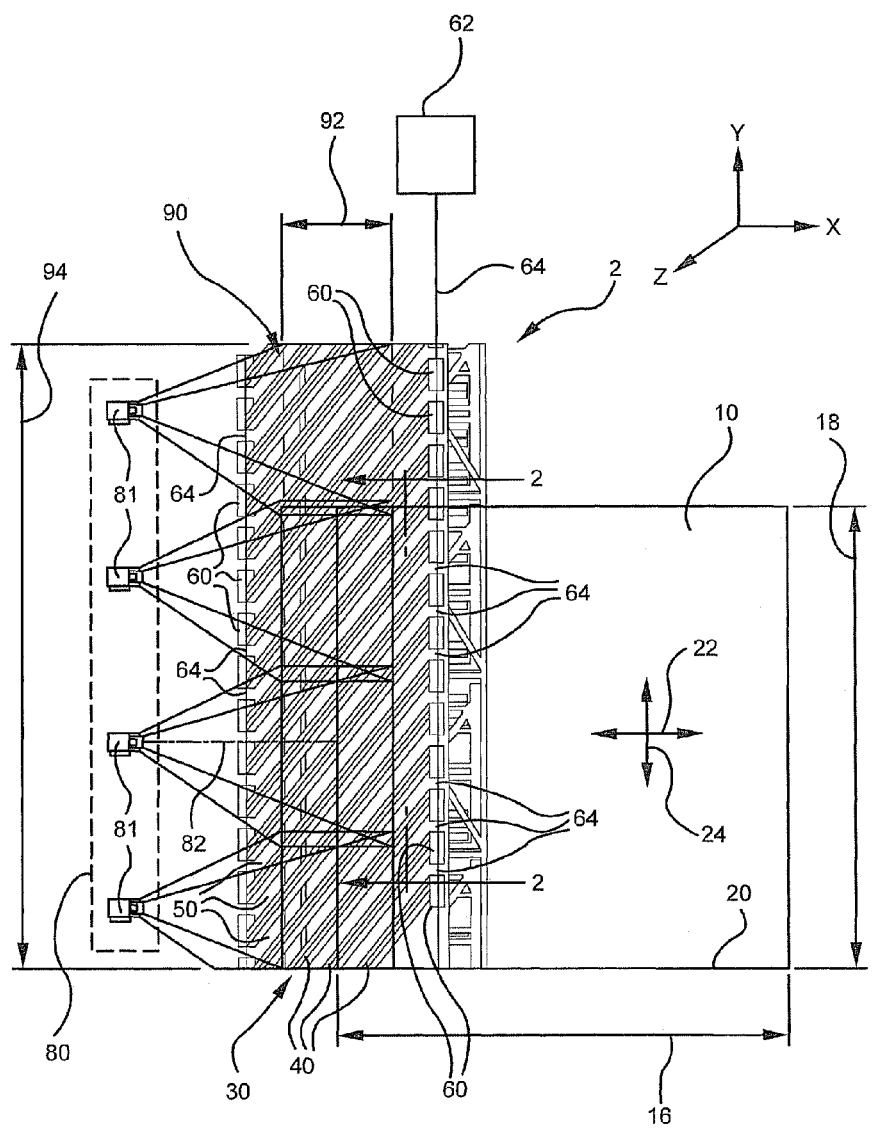
FIG. 1 is a schematic isometric view of a measurement apparatus according to one embodiment.

In the following detailed description, for purposes of explanation and not limitation, example embodiments disclosing specific details are set forth to provide a thorough understanding of the principles of the present invention. However, it will be apparent to one having ordinary skill in the art, having had the benefit of the present disclosure, that the present invention may be practiced in other embodiments that depart from the specific details disclosed herein. Moreover, descriptions of well-known devices, methods and materials may be omitted so as not to obscure the description of the principles of the present invention. Finally, wherever applicable, like reference numerals refer to like elements.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the singular forms "a," "an" and "the" include plural referents unless the context clearly dictates otherwise. Thus, for example, reference to a "component" includes aspects having two or more such components, unless the context clearly indicates otherwise.

References made to direction and/or orientation, for example right, left, horizontal, vertical, width, height, are made with respect to the figures as shown, only, and are in no manner intended to indicate absolutes.

In one embodiment, there is provided a support structure that allows measurement error induced by the support structure to be easily removed from a transmission mode measurement of process-induced features in a transparent sheet. The process-induced features may include thickness variation, cord, streak, discontinuities or inclusions in the sheet, and/or stress, for example. The support structure is configured and arranged so that when it supports a transparent sheet, the measurement error induced by the support structure is viewed by the imaging device as extending along or parallel to a first axis that is oblique to a second axis along or parallel to which the process-induced error in the transparent sheet extends when viewed by the imaging device. Because the support-structure-induced error is along an axis different from that along which the process-induced features are typically found, the support-structure-induced errors may easily be differentiated and removed from a sheet measurement.

Figure 2:
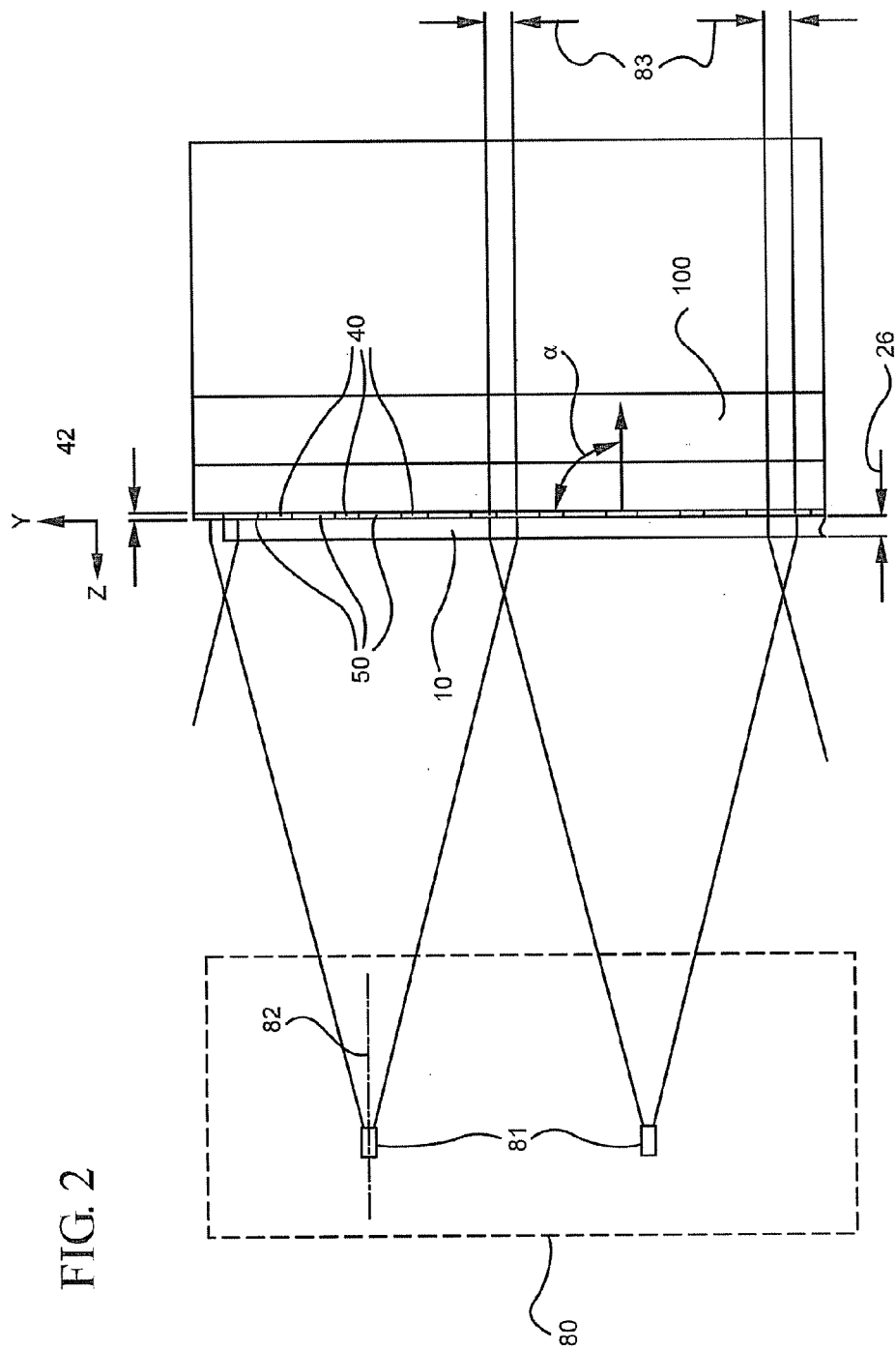
FIG. 2 is a schematic side view of the measurement apparatus of FIG. 1 as taken along line 2-2.

FIGS. 1 and 2 show one embodiment of an apparatus 2 for making transmission mode measurements of a transparent sheet 10, wherein the apparatus 2 includes a light source 100, an imaging device 80 having a viewing area 90, and a support structure 30 for holding the transparent sheet 10 as the transmission mode measurement is made.

The transparent sheet 10 includes a width 16, a height 18, an edge 20, and axes 22, 24. The axis 24 extends along the direction in which the sheet 10 was drawn, i.e., a down-draw direction. Although, strictly speaking, the sheet may be cut from a ribbon that is drawn, for ease in description the sheet may be described as being drawn with the understanding that it is actually the ribbon which is drawn, and the sheet is cut from that ribbon. The sheet 10 may be cut from a ribbon produced by a down-draw, slot-draw, up-draw, or float, process for example. The axis 22 extends along a direction perpendicular to that in which the sheet 10 was drawn, i.e., the cross-draw direction. As shown in FIGS. 1 and 2, the axis 22 extends in a direction along which the sheet 10 will be indexed, or moved, through the apparatus 2, which is preferred. Instead, however, the axis 24 may extend in the sheet-index direction. Additionally, as shown in FIG. 2, the sheet 10 includes a thickness 26. The transparent sheet may be glass for example, in particular glass used in making flat panel display units like LCDs, field emission devices, or plasma displays, for example. As shown in FIG. 1, the sheet 10 is in the X-Y plane.

Process-induced features (inclusions, thickness variations, cord, streak, and stress, for example) typically manifest themselves with an orientation similar to that in which the transparent sheet is drawn, i.e., along or generally parallel to axis 24. In other cases, some process-induced features may manifest themselves in a direction perpendicular to that in which the transparent sheet is drawn, i.e., in a cross-draw direction or along or generally parallel to axis 22.

Light source 100 (see FIG. 2) may be any suitable light source for making a transmission-mode measurement. For example, the light source 100 may be monochromatic light, laser light, an incandescent lamp, diffuse and/or collimated light, and may include any suitable wavelengths in the visible or invisible (to the human eye) range. When making stress measurements, for example, the light source would include a specific degree of polarization, whether linearly polarized or circularly polarized. The light source 100 should be of sufficient size to illuminate the viewing area 90 of the imaging device 80.

The imaging device 80 includes image capture units 81 that together cover a viewing area 90. The viewing area 90 includes a width 92 and a height 94 over which an image can be captured. Although the imaging device 80 is shown as including four image capture units 81 in FIG. 1, any suitable number of image capture units 81, including only one, may be used to suit a particular viewing area 90. For example, the number of image capture units 81 may depend on the image capture area for each individual image capture unit 81, the general size range of the sheets 10 to be inspected, and the desired processing speed. The image capture units 81 may include CCD or CMOS technology for example, and may be area or line scan type imaging devices, or PIN (Positive-Intrinsic-Negative) detectors, for example. Each image capture unit 81 has an optical axis 82, which may extend at any suitable angle with respect to the X-Y plane in which the sheet 10 is located. The image capture areas of adjacent image capture units 81 are shown as overlapping at 83 so a complete image of the sheet 10 may be taken by stitching the individual images together, however, there need not be any overlap 83. Although the image capture units 81 are shown as disposed in a vertical column, they may be disposed in any suitable arrangement, for example horizontally, or in an array, so as to define the viewing area 90.

For measuring stress in the sheet 10, for example, the image capture units 81 may be optical stress measurement sensors which provide capability to measure in-plane stress and optical retardation across a defined region. The light source 100 may be aligned with the stress measurement sensor to create a circularly polarized and uniform light distribution that is transmitted through the sheet 10 and onto the sensor for analysis of the stress distribution in the sheet 10.

The support structure 30 is disposed between the light source 100 and the imaging device 80, so as to hold the sheet 10 during transmission-mode measurements. The support structure 30 includes bars 40, spaces 50, and a pressure/vacuum source 62. The bars 40 are separated from one another by intervening spaces 50.

Figure 3:
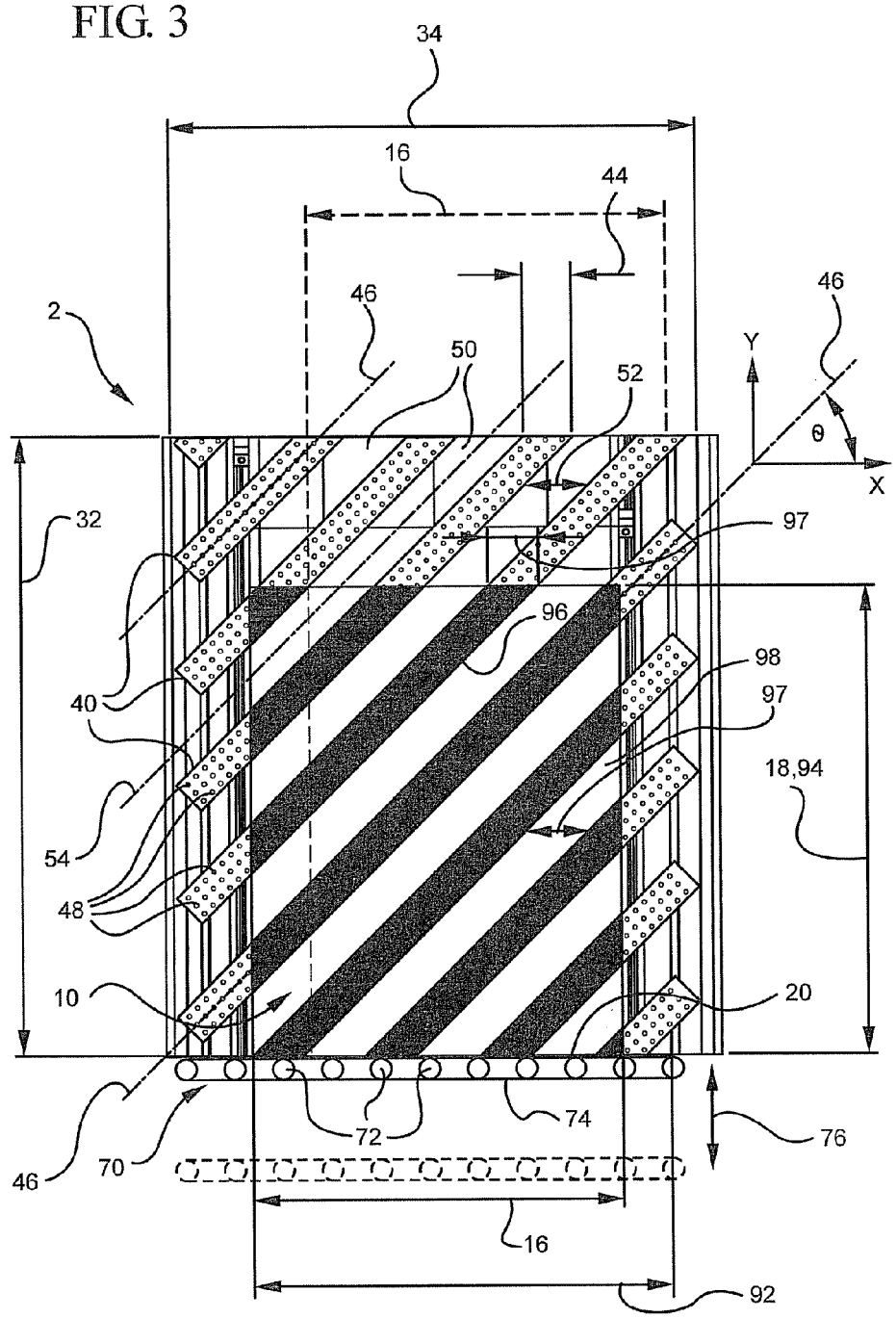
FIG. 3 is a schematic view of a support structure and a conveyance device that may form a part of a measurement apparatus.

Reference will now be made to FIG. 3 to explain features of the bars 40 and spaces 50 in more detail. It should be noted, however, that between FIGS. 1 and 3, the width 16 and height 18 of the sheet 10 are shown in different proportion to the width 92 and height 94 of the viewing area 90. Each of the bars 40 includes a width 44 taken parallel to the X-axis, and a longitudinal axis 46 that is oblique to the X-axis (and thus also oblique to the axis 22). Specifically, the axis 46 forms an angle θ with the X axis. The angle θ may be any suitable value so that the axis 46 is oblique to the X-axis (and thus also to the axis 22). The value of angle θ will influence the direction of the support-structure induced errors seen by the imaging device 80. The more the axis 46 becomes closer to parallel to the axis 22, the more the support-structure-induced errors will look like process-induced features extending parallel to axis 22, and the harder it will be to separate the two. Similarly, the more the axis 46 becomes closer to parallel to the axis 24, the more the support-structure-induced errors will look like process-induced features that extend parallel to axis 24, and also harder to separate the two. For example, in one embodiment the angle θ may be 25 to 65 degrees, in another embodiment the angle θ may be 35 to 55 degrees, and in still another embodiment the angle θ may be such that the bars form substantially a diagonal of either one or both of: i) the image capture unit's 81 image capture area, e.g., about 45 degrees for a square image capture area; and ii) the viewing area 90, e.g., about 45 degrees for a square viewing area 90. With the angle θ in the foregoing ranges, the apparatus 2 will work when process-induced features of interest are formed either along the down-draw axis 24 or cross-draw axis 22. That is, the apparatus 2 is insensitive to sheet orientation being landscape or portrait. Similarly to the bars 40, each of the spaces 50 includes a width 52 taken parallel to the X-axis, and a longitudinal axis 54 that is oblique to the X-axis (and thus also to the axis 22).

When the bars 40 are used to hold a sheet 10, they will influence the transmission-mode measurement of the process-induced feature in interest. Without wishing to be bound by any particular theory of how the bars influence the transmission-mode measurement, applicants offer the following. The bars 40 present a planar surface for holding the sheet 10, and thus change the shape of the sheet 10 when held. The bars 40 may be air bars for forming an air cushion to support the sheet 10, vacuum bars that vacuum the sheet 10 against the bars 40, or pressure/vacuum bars that may apply both a pressure and a vacuum. When the bars 40 are pressure/vacuum bars, they may either apply both pressure and vacuum at the same time to form an air cushion, or may sequentially apply pressure and vacuum as when using pressure to form an air cushion for transportation and using vacuum to hold the sheet 10 against the bars 40. The bars 40 include openings 48 through which gas, air for example, under pressure and/or vacuum may pass, and are coupled to a pressure/vacuum source 62 by plenums 60 and conduits 64. The specific manner of coupling each bar 40, and its openings 48, to the pressure/vacuum source 62 is not a part of the present invention and may include any known technique. In any case, through the use of pressure and/or vacuum, the bars 40 exert a holding force on the sheet 10, wherein the holding force causes the sheet 10 to take on a planar configuration, as noted above, which changes the shape of the sheet 10.

By changing the shape of the sheet 10, the bars 40 induce an error in the measurement of the process-induced feature in the sheet 10 that will be imaged by the imaging device 80. Because the longitudinal axes 46 of the bars 40 are oblique to the axes 22 and 24 of the sheet 10, the support-structure-induced errors will appear in the image as oblique to the process-induced features of interest in the sheet 10. Similarly, because the longitudinal axes 54 of the spaces 50 (through which the light from light source 100 passes to imaging device 80) are oblique to the axes 22 and 24 of the sheet, any support-structure-induced errors due to overlap/stitching will appear in the image as oblique to the process-induced features of interest in sheet 10. Accordingly, through typical image/data processing techniques, the support-structure-induced errors will be easy to remove, thereby giving a more accurate picture of the process-induced features.

Having the longitudinal axes 46 of the bars 40 oblique to the axes 22, 24 provides benefits other than those mentioned above. Specifically, this arrangement makes the support structure 30, particularly widths 44, 52, largely insensitive to the width 16 and height 18 of the sheet 10. Additionally this arrangement provides adequate support near the edges of the sheet 10 as it is being measured. That is, if the support included bars 40 that were either parallel to axis 22 or to axis 24, an entire longitudinal edge of the sheet 10 would be unsupported as it was being imaged, thereby leading to possible measurement error.

Vacuuming the sheet 10 to the bars 40 may provide additional advantages as follows. First, the sheet 10 will be provided in a well-defined fixed Z-axis position, i.e., the plane defined by the surfaces of the bars 40. This arrangement may facilitate set-up of the measurement apparatus 2 and, in particular, the imaging device 80. Additionally, or alternatively, this arrangement may reduce measurement error introduced by positional variation in the sheet 10 as images are taken. Further, vacuuming the sheet 10 to the bars 40 provides an easier sheet to sheet comparison because each sheet will be held in a known condition. Second, taking an image of the sheet 10 when in this condition offers the advantage of providing a measurement of the feature in interest as it will exist in a panel assembly or other display manufacturing process wherein the sheet 10 is made flat.

Moreover, the orientation of the sheet 10 relative to horizontal may influence the support-structure-induced errors seen by the imaging device 80. As shown in FIG. 2, the bars 40 may be provided in an arrangement so that the sheet 10 is held in the X-Y plane. Alternatively, the bars 40 may be disposed so as to hold the sheet 10 at any suitable angle α with respect to the Z axis. That is, the sheet 10 may be held in a vertical orientation, for example a being 90 degrees as shown (sheet 10 in the X-Y plane), or at any successively smaller angle α down to 0 degrees, i.e., in a horizontal orientation (sheet 10 in the X-Z plane). However, a smaller value of α is preferred, because as α increases toward 90 degrees, the transparent sheet 10 may be subjected to sag due to gravity (depending upon the width 52 of the spaces 50, and the stiffness of the sheet 10).

As shown in FIG. 3, the support structure 30 may also include a conveyance device 70. The conveyance device 70 includes rollers 72 and a belt 74 for contacting the edge 20 of the sheet 10. The belt 74 may be driven by the rollers 72 to move, or index, the sheet 10 through the measurement apparatus 2 so that successive images of the sheet 10 may be taken; the successive images being stitched together to form a full-sheet measurement. The conveyance device 70 can be moved from the position shown in the solid lines in FIG. 3 to that shown in dashed lines, as necessary by any suitable mechanism known in the art. Accordingly, the conveyance device 70 may contact, or be moved away from, the edge 20 when the sheet 10 is imaged. On one hand, the conveyance device 70 may support the sheet edge 20 during imaging, and can quickly move the sheet 10 through the measurement apparatus 2 when left in place. However, on the other hand, the conveyance device 70 contacting the sheet edge 20 may induce positional error to the sheet 10 thereby reducing accuracy of the measurement. Thus, it may be beneficial to move the conveyance device 70 to a position away from the sheet 10 during imaging. Although a belt and roller device is shown as the conveyance device 70, any suitable device may be used. For example, the conveyance device may include a grippers, a suction chuck, and/or a robotic arm.

Further, as shown in FIG. 3, the relative size of the support 30 and viewing area 90 may facilitate reducing the time needed to make a full-sheet measurement. In fact, with the right proportions, a full-sheet measurement may be made with as little as two overlaid images from the imaging device 80. The support 30 includes a width 34 and a height 32. Similarly, the viewing area 90 includes a width 92 and a height 94, whereas the sheet 10 includes a width 16 and a height 18, and the bars 40 each include a width 44. For example, two images from the imaging device 80 are sufficient to obtain a full-sheet measurement when: the height 94 is equal to or larger than the sheet height 18; and the width 92 is larger than the sheet width 16 by at least the width 44. As shown in FIG. 3, the support height 32 and width 34 are equal to or larger than the sheet width 16 and height 18, which may be the case to promote increased accuracy and speed in measurement for smaller sheet sizes, but they need not be. It should be noted that, in the foregoing discussion, the width 44 was used as a surrogate for the width 97 of the blocked areas 96, i.e., the areas in the viewing area 90 that will not be imaged by the imaging device 80 because they are blocked by the bars 40. However, this may not necessarily be the case. That is, depending upon the angle of the optical axis 82 relative to the plane in which the bars 40 lie (which in turn depends upon the angle α), the thickness 42 of the bars 40, and the edge profile of the bars 40, the width 97 may be greater than the width 44 (similarly, the width 99 of the imagable areas 98 may be less than the width 52 of the spaces 50). Nonetheless, the width 44 provides a minimum amount by which the width 92 must exceed the width 16 to obtain a full-sheet measurement with only two images.

The structure that brings the sheet 10 to the measurement apparatus 2, particularly to the support structure 30, is not particularly limited, and may be any suitable structure, for example, a bottom conveyor, an overhead contact mechanism, a suction chuck, a gripper, a robotic arm, and/or fluid bearing bars.

Figure 4:
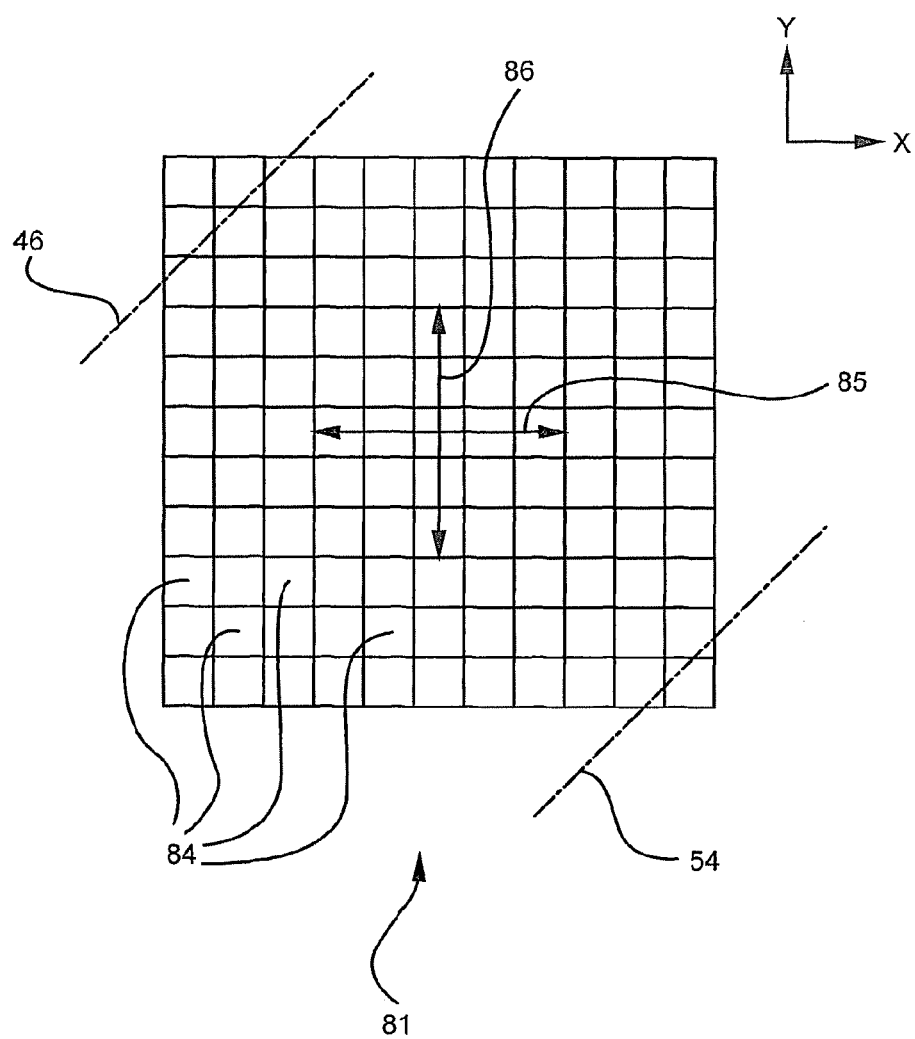
FIG. 4 is a schematic view of a pixel array of an image capture unit that may form a part of a measurement apparatus, and includes axes of support structure features superimposed thereon.

FIG. 4 is a schematic view of one possible arrangement of a pixel array for one image capture unit 81, and includes the axes 46 and 54 superimposed on the pixel array. As shown in this figure, the image capture unit 81 has a two-dimensional array of pixels 84 arranged along axes 85 and 86. The image capture unit 81 is positioned relative to the support structure 30 and the sheet 10 so that axes 85 and 86 are parallel to axes 22 and 24 of the sheet (corresponding to the X and Y axes), but are oblique to axes 46 and 54.

Operation of the measurement apparatus 2 will now be described.

A first scenario will be described with reference to FIG. 3, wherein the sheet height 18 is equal to or smaller than the height 94 of the viewing area, and the sheet width 16 is smaller than the width 92 of the viewing area by at least the width 44 of a bar 40. In this instance, a full-sheet measurement can be made with as little as two images from the imaging device 80, and may be done as follows. The sheet 10 is loaded onto the support 30 so that width 16 is at the dashed-line position. As seen from FIG. 3, the width 16 (dashed-line position) is within the width 92. With the sheet 10 at this position, the imaging device 80 captures a first image of the sheet 10, and will include the imagable areas 98 (areas shown in white), but not the blocked areas 96 (areas shown in black) adjacent to the bars 40. Next, the sheet 10 is indexed, by the amount of one blocked-area width 97 so that the width 16 is in the position shown in solid lines, which is still within the width 92 of the viewing area 90. As can be seen from a comparison of the sheet having the positions indicated by the dashed and solid line positions of width 16, areas 96 that were previously blocked may now be imaged and, similarly, previously imagable areas 98 would then be blocked. With the sheet 10 at this position (width shown in solid line), the imaging device 80 captures a second image of the sheet 10. The first and second images may then be combined using techniques known in the art to form a full-sheet measurement. As shown and described above, the sheet 10 would be indexed through the measurement apparatus 2 in the negative X direction. Alternatively, the sheet 10 could be indexed in the positive X direction from the solid-line position to the dashed-line position. In either case, the sheet 10 could be indexed, or moved, by the conveyance device 70.

Figure 5:
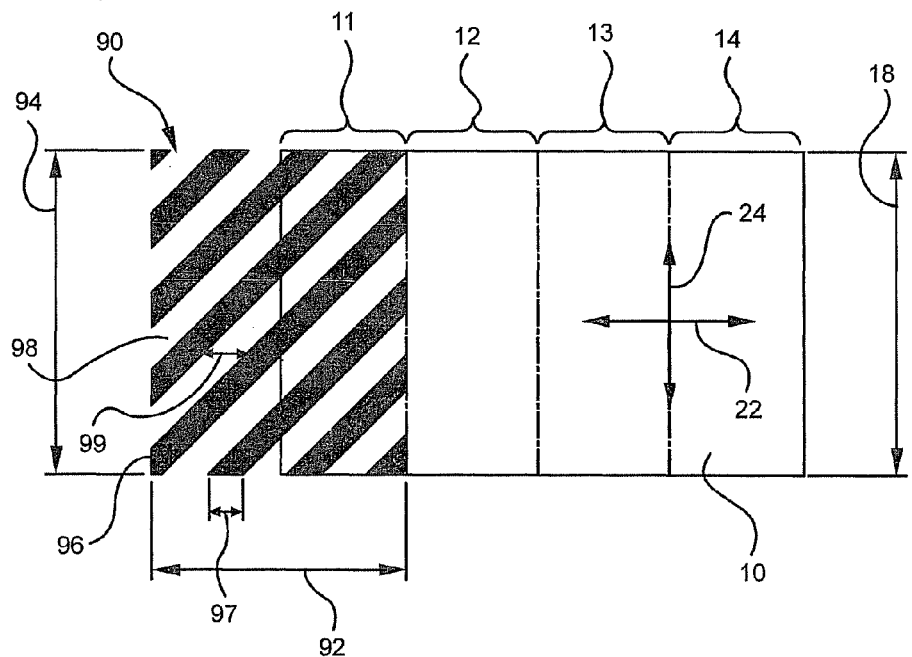
FIG. 5 is a schematic view of a transparent sheet relative to a viewing area of an imaging device.
Figure 6:
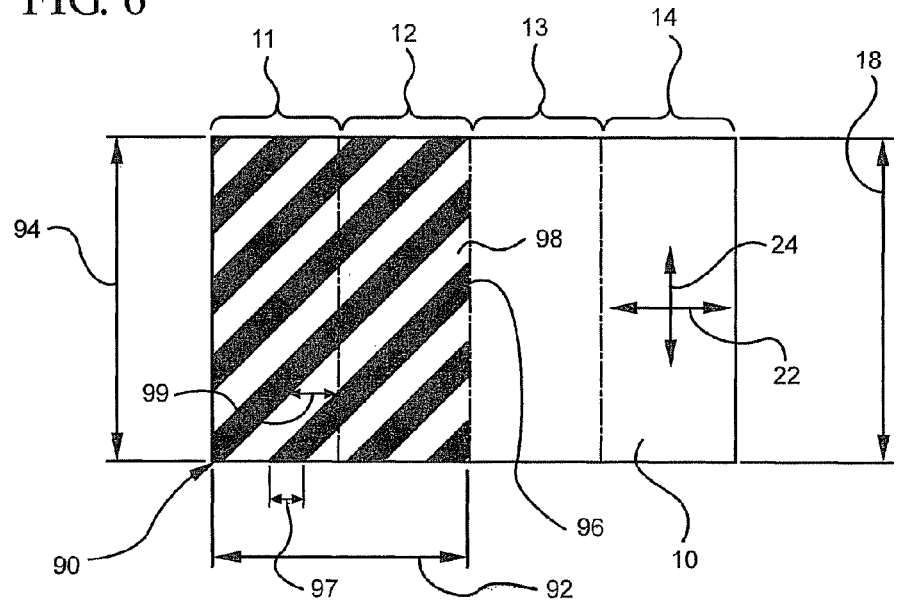
FIG. 6 is a schematic view of a transparent sheet relative to a viewing area of an imaging device, showing a position of the transparent sheet indexed from its position shown in FIG. 5.

Another scenario will be described with reference to FIGS. 5 and 6, wherein the width 16 of the sheet 10 is greater than the width 92 of the viewing area 90, and the height 18 of the sheet 10 is equal to the height 94 of the viewing area 90. This case is similar to that shown in FIG. 1, for which a process similar to that described below in connection with FIGS. 5 and 6 may be used to obtain a full-sheet measurement; the difference being that in FIG. 1, the height 94 of the viewing area 90 is larger than the height 18 of the sheet 10, whereas in FIGS. 5 and 6, the height 94 of the viewing area 90 is equal to the height 18. The viewing area 90 includes blocked areas 96, each having a width 97, and imagable areas 98, each having a width 99. The image capture devices 81 will obtain an image of the sheet 10 over the imagable areas 98, but will not obtain an image of the sheet 10 over the blocked areas 96. The arrangement of the support 30 (including bars 40, width 44, thickness 42, angles α and θ), imaging device 80 (including optical axis 82), is such that the width 99 is greater than or equal to the width 97. Having a width 99 greater than width 97 facilitates stitching in that the images will contain some overlapping areas of the sheet 10. In the case shown in FIGS. 5 and 6, more than two images will need to be taken and stitched together to provide a full-sheet measurement, and the images may be obtained as follows.

The sheet 10 is divided into phantom sections each of approximately the same width as the others, and each having a width approximately half that of the width 92 of the viewing area; in this case $1^{st}$ through $4^{th}$ sections 11, 12, 13, and 14. The first section 11 is disposed in the right-half of the viewing area 90, and a first image is taken; this first image includes data from the imagable areas 98, which is approximately half the area of section 11. See FIG. 5. The sheet 10 is then indexed, or moved, so that both sections 11 and 12 are within the viewing area 90, with the section 11 in the left half and the section 12 in the right half, and a second image is taken with the imaging device 80. See FIG. 6. At this point, the full area of section 11 has been imaged, with half the data included in each of the first and second images, and approximately half of the area of section 12 has been imaged. The sheet is then again indexed so that both sections 12 and 13 are in the viewing area 90, with the section 12 in the left half and the section 13 in the right half, and a third image is taken with the imaging device 80. At this point, the full area of section 12 has been imaged, with half the data included in each of the second and third images, and approximately half of the area of section 13 has been imaged. The process then continues this series of imaging and indexing until the section 14 lies within the left half of the viewing area 90, and a fifth image is taken. The first through fifth images are then stitched together, using techniques known in the art, to obtain a full-sheet measurement of the process-induced feature in interest. If a particular sheet width is not an even multiple of half the width 92, the sheet can be divided into equal half-width sections with the remainder in one or more sections at either end of the sheet width 16.

The time necessary to obtain a full-sheet measurement can be minimized by choosing an appropriate balance between the size of the support 30, the viewing area 90, the sheet 10, the imagable areas 98, and the blocked areas 96.

For example, on a macro scale, the larger the viewing area width 92 and/or height 94 with respect to the corresponding sheet 10 width 16 and/or height 18, the fewer the number of overlapping images that will need to be taken and, thus, the shorter the processing time.

On a more detailed level, having the width 99 of the imagable areas 98 larger than the width 97 of the blocked areas 96 will facilitate shorter processing times because a full-sheet view may be constructed with as few images as possible. However, if the width 99 (width 52) becomes too much larger than the width 97 (width 44) then there may not be adequate support for the sheet 10 to make an accurate measurement. That is, in such a case, the support 30 will not be adequate enough to hold the thin sheet steady, and in a consistent/constant plane, for measurement. The widths 44 and 52 (taken together with the value of angle θ, the angle the optical axis 82 makes with the X-Y plane, and the thickness 42, as noted above) influence the widths 97, 99. Accordingly, for ease of description, the widths 44 and 96 may be used interchangeably, whereas the widths 52 and 99 may be used interchangeably with the understanding that this may not be strictly the case.

In other words, the relative widths 44 and 52 influence the ratio of supported/blocked area 96 to unsupported/imagable area 98 and, in turn, also influence the number of times a sheet may need to be imaged in order to provide a full-sheet measurement. In order to facilitate stitching images together to provide a full-sheet measurement, it is preferable to have some overlap between the images that will be stitched. Additionally, it is preferable to image a complete section of a sheet with only two images to speed processing time. Accordingly, it is beneficial to have the widths 44 less than or equal to the widths 52 (similarly having the widths 97 less than or equal to the widths 99). Although all of the widths 44 are shown as being the same, they need not be. Similarly: although all of the widths 52 are shown as being the same, they need not be; although all of the widths 96 are shown as being the same, they need not be; and although all of the widths 98 are shown as being the same, they need not be.

It should be emphasized that the above-described embodiments of the present invention, particularly any "preferred" embodiments, are merely possible examples of implementations, merely set forth for a clear understanding of principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

For example, although the support 30 is shown on only one side of the transparent sheet 10, as in FIG. 2, supports 30 could be disposed on both sides of the sheet 10.

What is claimed is:

1. An apparatus, for measuring process-induced features in a transparent sheet, comprising:
   a light source;
   an imaging device; and
   a transparent-sheet support structure disposed between the light source and the imaging device,
   wherein the support structure is configured and arranged to support a transparent sheet so that measurement error induced by the support structure is viewed by the imaging device as extending along or parallel to a first axis that is oblique to a second axis along or parallel to which the process-induced features in the transparent sheet extend when viewed by the imaging device.

2. The apparatus of claim 1, wherein the process-induced feature comprises stress.

3. The apparatus of claim 1, wherein the support structure includes bars extending along axes oblique to the second axis.

4. The apparatus of claim 3, wherein the bars include openings, and the support includes a vacuum source in communication with the openings.

5. The apparatus of claim 3, wherein spaces are disposed between the bars, wherein the bars include a first width and the spaces include a second width, and further wherein the first width is less than or equal to the second width.

6. The apparatus of claim 1, wherein the imaging device includes pixels oriented along a third axis, wherein the support structure includes spaces through which light from the light source may be viewed by the imaging device, the spaces including longitudinal axes parallel to the first axis, and further wherein the third axis is oblique to the longitudinal axes.

7. A method of measuring process-induced features in a transparent sheet, comprising:
   disposing a transparent sheet on a support structure that is disposed between a light source and an imaging device;
   supporting the transparent sheet so that measurement error induced by the support structure is viewed by the imaging device as extending along or parallel to a first axis that is oblique to a second axis along or parallel to which the process-induced features in the transparent sheet extend when viewed by the imaging device;
   capturing a first image of a first section of the transparent sheet;

moving the transparent sheet and then capturing a second image of the first section of the transparent sheet; and combining the first and second images to form an image of the process-induced features in the first section of the transparent sheet.

8. The method of claim 7, wherein the first and second images together cover the entire area of the first section of the transparent sheet.

9. The method of claim 8, wherein the first section of the transparent sheet encompasses the entire area of the transparent sheet.

10. The method of claim 7, further comprising contacting the transparent sheet with a conveyance device during the step of moving, but not during the steps of capturing the first and second images.

11. The method of claim 7, further comprising flattening the transparent sheet prior to the steps of capturing the first and second images, and maintaining the transparent sheet in the flattened condition during the steps of capturing the first and second images.

12. The method of claim 11, wherein the step of flattening comprises vacuuming the transparent sheet against the support structure.

13. The method of claim 7, wherein the step of combining further comprises removing the measurement error induced by the support structure.

14. The method of claim 7, wherein the support structure includes bars extending along axes oblique to the second axis, wherein spaces are disposed between the bars, wherein the bars include a first width and the spaces include a second width, and further wherein the first width is less than or equal to the second width.

15. The method of claim 14, wherein the imaging device is capable of capturing an image within a viewing area having a third width, the transparent sheet includes a fourth width, and wherein the third width is larger than the fourth width by an amount equal to or greater than the first width.

16. The method of claim 15, wherein the support structure includes a fifth width, and the fifth width is larger than the fourth width by an amount equal to or greater than the first width.

17. The method of claim 14, wherein the transparent sheet is moved in a transportation direction relative to the support structure, and wherein the axes of the bars form an angle with the transportation direction, the angle ranging from 25 to 65 degrees.

18. The method of claim 7, wherein the transparent sheet is moved in a direction parallel or perpendicular to the second axis.

19. The method of claim 7, wherein the imaging device includes pixels extending along a third axis, and further wherein the third axis is oblique to the first axis.

20. The method of claim 7, wherein the process-induced feature comprises stress.

* * * * *

UNITED STATES PATENT AND TRADEMARK OFFICE
CERTIFICATE OF CORRECTION

| | | |
|---|---|---|
| PATENT NO. | : 8,260,028 B2 | |
| APPLICATION NO. | : 12/607346 | |
| DATED | : September 4, 2012 | |
| INVENTOR(S) | : Richard Sean Priestley et al. | |

It is certified that error appears in the above-identified patent and that said Letters Patent is hereby corrected as shown below:

ON THE TITLE PAGE:

Item (75) Inventors: "Richard Sean Priestly" should be -- Richard Sean Priestley --

Signed and Sealed this
Eleventh Day of December, 2012

David J. Kappos
*Director of the United States Patent and Trademark Office*